July 6, 1948. E. PRUSHEK Plant Pat. 802
CHRYSANTHEMUM PLANT
Filed Nov. 29, 1946
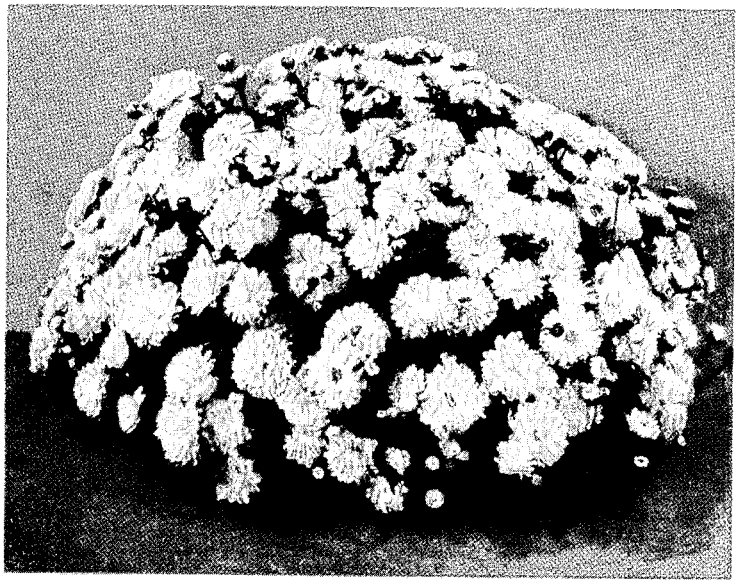
Emil Prushek
Inventor
By Robb & Robb
Attorneys Patented July 6, 1948

Plant Pat. 802

UNITED STATES PATENT OFFICE

802

CHRYSANTHEMUM PLANT

Emil Prushek, Niles, Mich., assignor to The R. M. Kellogg Company, Three Rivers, Mich., a corporation of Michigan Application November 29, 1946, Serial No. 712,882

1 Claim. (Cl. 47—60)

My present invention comprises a new and distinct variety of chrysanthemum plant, the result of a cross between the well-known variety "Red Cushion" and an unnamed chrysanthemum seedling.

The object of my invention, in general, was to produce a new variety of chrysanthemum of much more dwarf and compact characteristics or habits of growth of the plant than previous varieties; and also to produce such dwarf and compact variety of chrysanthemum having certain desirable characteristics in reference to earlier flowering and longer season, and longer and more consistent color life.

To the foregoing end I have conducted a program of careful selection and cross-breeding with the view of producing new varieties of chrysanthemum of much more dwarf and compact habits of growth in different desired colors in reference to the blooms of such plants.

The result of the specific hybridization above mentioned has been to produce my present new and distinct variety of chrysanthemum characterized by its more dwarf and compact habits of growth, its early flowering, its long season due to the long color life of the individual blooms, and the succession of blooms by which new flowers cover the older ones, and also characterized by the deeper yellow color of the bloom of my new variety.

A comparison of my new variety with its parent "Red Cushion" illustrates strikingly the characteristic of dwarfness of my new variety. Roughly, my new variety has about half the dimension measurements of the standard cushion varieties of chrysanthemums, which means that my new variety has about one-eighth of the cubic mass of the standard varieties in its class. More specifically, the height of plants of my new variety ranges from 8" to 10", and the breadth ranges from 14" to 18", in reference to plants grown in fields in the region of Niles, Michigan.

Plants of the parent variety, "Red Cushion," grown in fields in the same region average 18" in height and 26" in breadth. The unnamed seedling parent of the present new variety had certain of the desired characteristics in reference to the dwarf and compact habit of growth, for which reason it was selected for purposes of the specific hybridization above mentioned which produced the present new variety.

In regard to the early blooming habit of my new variety, it may be mentioned that the average time of opening of the blooms of my new variety in the region above mentioned is around September 25th, and the average date of full bloom is about September 30th. This is fully ten days to two weeks earlier than the respective opening and full bloom dates of standard varieties of cushion chrysanthemums.

The average length of blooming season of my new variety extends from about September 25th to freezing weather.

Of the old varieties of chrysanthemums, "Harvest Gold" is the one most nearly like my new variety. However, my new variety is unlike "Harvest Gold" in reference to its distinctive dwarf and compact habit of growth, its earlier blooming characteristics, and longer season. The color of my new variety is a deeper yellow and holds up longer than the lighter yellow of "Harvest Gold." The individual blooms of my new variety are of better form and substance, being a near approach to pompons compared with the softer, looser blooms of "Harvest Gold."

My new variety has been found to retain its distinctive characteristics through successive asexual reproduction.

A typical plant of my new variety of chrysanthemum is shown in the accompanying drawing forming a part hereof.

The following is a detail description of my new variety of chrysanthemum plant, the color references being to the Horticultural Colour Chart of the British Colour Council:

Classification: Botanic—*Chrysanthemum hortorum.*

*Flower*

Blooming habit: Blooms early; profusely. Recurrent—continuous in the fall.

Bud:

*Size.*—Small.

*Form.*—Short with flat top; globular.

Is not affected by wet weather.

Is not affected by hot weather.

*Color.*—When sepals first divide—Sulphur Yellow 1/1. When petals begin to unfurl—Aureolin Yellow 3. When half blown: inside of petals—Dresden Yellow 64; reverse of petals—Dresden Yellow 64/1.

(All color references are to the Horticultural Colour Chart of the British Colour Council.)

*Calyx.*—Shape—funnel. Size—broad; small. Aspect—smooth.

*Peduncle.*—Medium length. Aspect—rough. Color—medium green. Strength—bending; slender.

*Opening.*—Bud opens well and is not affected by hot or wet weather.

Bloom:

*Size.*—Small.

*Average size when fully expanded.*—1¾".

*Borne.*—Singly.

*Stems.*—Medium—normal.

*Form.*—When first open—flat. Permanence—retains its form to the end.

*Petalage.*—Very double.

*Number of petals.*—Under normal conditions—several hundred.

*Color.*—Center of flower—Aureolin Yellow 3. *Outer petals*—Dresden Yellow 64/1. Inside of petals—Dresden Yellow 64/1. Base of petals—Uranium Green 63/1. Reverse of petals—Dresden Yellow 64/2.

*Discoloration.*—First week — none. Second week—a fading to Sulphur Yellow 1/1.

(All color references are to the Horticultural Colour Chart of the British Colour Council.)

Petals:

*Texture.*—Thin, soft. Slight fading by wet weather. Not affected by hot weather.

*Appearance.*—Velvety inside, shiny outside.

*Form.*—Oval.

*Arrangement.*—Imbricated.

*Lastingness.*—Very long.

Genital organs:

*Stamens, anthers.*—Small, few.

*Color.*—Yellow.

*Stamens, filaments (threads).*—Short. *Color*—lemon yellow.

*Pollen.*—Gold yellow.

*Stigmas.*—Yellow.

Form: Bush.

Growth: Medium; dwarf; compact.

Foliage:

*Size.*—Small.

*Quantity.*—Normal.

*Color (new foliage).*—Upper side—normal green; under side—light green.

*Color (old foliage).*—Upper side — dark green; under side—normal green.

*Shape.*—Oval, acutely lobed.

*Texture.*—Velvety, flat on upper side.

*Texture.*—Rough on under side.

*Ribs and veins.*—Light.

*Edge.*—Serrated.

*Serration.*—Double, small.

*Leaf stem.*—Green; under side—rough.

*Stipules.*—Short, smooth.

Wood:

*New wood.*—Color—light green.

*Old wood.*—Color—brown.

I claim:

A new and distinct variety of chrysanthemum plant substantially as herein disclosed, characterized as to novelty by its dwarf, compact growth, its early flowering, its long blooming season, the long color life of its blooms, its production of a succession of blooms by which new flowers cover the older ones, and the deeper yellow color of its blooms as compared with the "Harvest Gold" variety.

EMIL PRUSHEK.